(12) United States Patent
Raines, Jr.

(10) Patent No.: US 7,922,730 B2
(45) Date of Patent: Apr. 12, 2011

(54) SUBTALAR ARTHROERESIS IMPLANT TRIAL SYSTEM

(75) Inventor: Aaron T. Raines, Jr., Dallas, TX (US)

(73) Assignee: Osteomed L.P., Addison, TX (US)

( * ) Notice: Subject to any disclaimer, the term of this patent is extended or adjusted under 35 U.S.C. 154(b) by 1561 days.

(21) Appl. No.: 11/219,603

(22) Filed: Sep. 1, 2005

(65) Prior Publication Data

US 2006/0004378 A1    Jan. 5, 2006

Related U.S. Application Data

(63) Continuation-in-part of application No. 10/777,514, filed on Feb. 11, 2004.

(51) Int. Cl.
*A61B 17/58* (2006.01)

(52) U.S. Cl. ........................................ 606/104; 606/916

(58) Field of Classification Search ............... 606/86 R, 606/99, 301, 321; 81/451–455, 461, 436; 411/411, 414, 415, 424, 426; 29/750
See application file for complete search history.

(56) References Cited

U.S. PATENT DOCUMENTS

| | | | | |
|---|---|---|---|---|
| 2,549,397 A | * | 4/1951 | Sparks | 403/328 |
| 4,450,591 A | | 5/1984 | Rappaport | 3/1.9 |
| 4,759,122 A | * | 7/1988 | Weintraub | 29/750 |
| 5,353,667 A | * | 10/1994 | Wilner | 81/436 |
| 5,364,400 A | * | 11/1994 | Rego et al. | 606/304 |
| 6,077,267 A | * | 6/2000 | Huene | 606/916 |
| 6,168,631 B1 | | 1/2001 | Maxwell et al. | 623/21.18 |
| 6,565,573 B1 | * | 5/2003 | Ferrante et al. | 606/62 |
| 6,589,245 B1 | * | 7/2003 | Weiler et al. | 623/13.14 |

OTHER PUBLICATIONS

Kinetikos Medical Incorporated, "KMI the Small Bone Specialist," Subtalar MBA Implant, 3 pages http://www.visitkmi.com/mba.html.
Sgarlato Labs, "LSI Implant—Lundeen Subtalar Implant," 3 pages, http://www.sgarlatolabs.com/products_lsi_implant.shtml.
Integra LifeSciences Corporation, Kalix, "Surgical Technique, Flat Foot Implant," 8 pages.
Stephen Smith, M.D., Extremities Solutions, "Sta-Peg," Subtalar Arthrorosis Implant, Smith Design, Surgical Technique, 12 pages.
Futura BioMedical, "Conical Subtalar Implant," 2 pages http://www.futurabiomedical.com/cs.html.
Kerry (nmi) Zang, DPM et al., U.S. Appl. No. 10/777,514, entitled "Conical, Threaded Subtalar Implant," Filed Feb. 11, 2004.

* cited by examiner

*Primary Examiner* — Thomas C Barrett
*Assistant Examiner* — Nicholas Woodall
(74) *Attorney, Agent, or Firm* — Baker Botts L.L.P.

(57) ABSTRACT

In accordance with a particular embodiment of the present invention, an implantation tool includes an elongate inner shaft having first and second ends. The tool also includes a first post coupled to the elongate inner shaft proximate the first end of the elongate inner shaft. The first post is configured to engage with a component to couple the component with the elongate inner shaft. The tool further includes a hollow outer shaft defining a longitudinal axial bore within which the elongate inner shaft is disposed. The hollow outer shaft is able to slide along the elongate inner shaft from a first longitudinal position to a second longitudinal position. The hollow outer shaft includes a first locking arm. Moving the hollow outer shaft from the first longitudinal position to the second longitudinal position moves the locking arm closer to the first post.

16 Claims, 6 Drawing Sheets

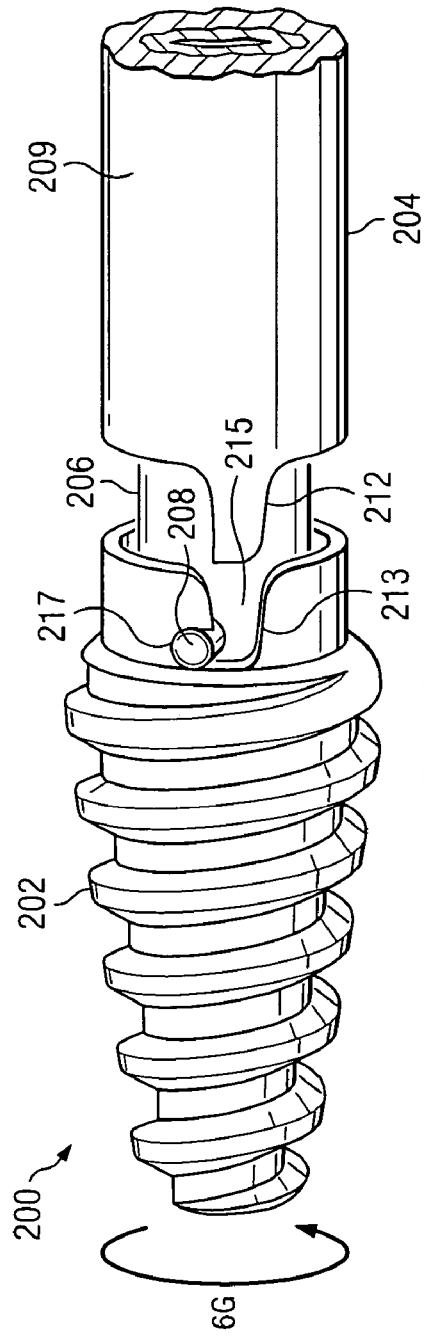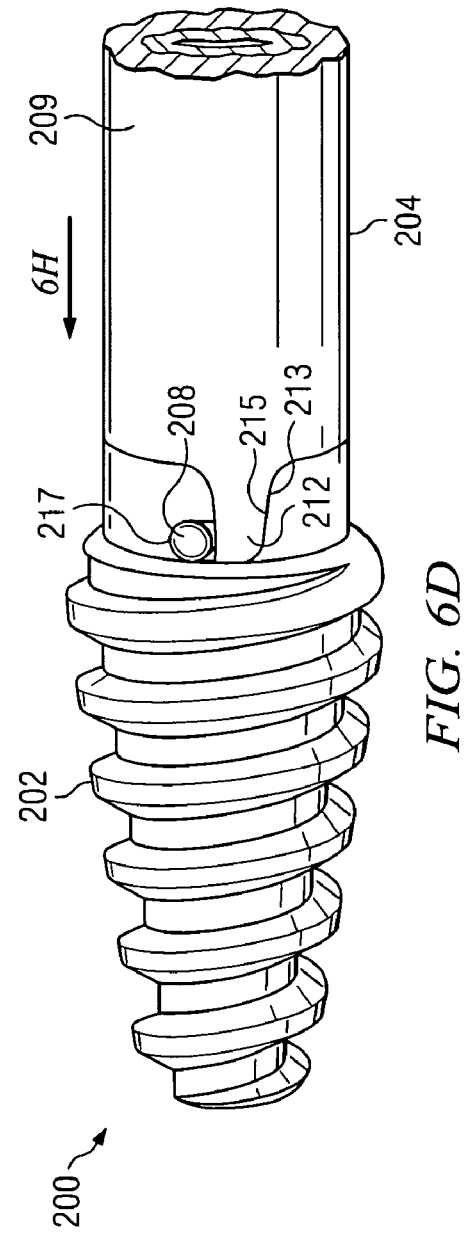

SUBTALAR ARTHROERESIS IMPLANT TRIAL SYSTEM

RELATED APPLICATIONS

This application claims priority benefit as a Continuation-in-Part of U.S. application Ser. No. 10/777,514, entitled "Conical, Threaded Subtalar Implant," filed Feb. 11, 2004.

TECHNICAL FIELD OF THE INVENTION

This invention relates generally to biomedical implants and in particular to a subtalar arthroeresis implant trial system.

BACKGROUND

Pes planus, or pes valgo planus, is a deformity producing a severe flat foot. The deformity occurs largely at one particular joint, the talocalcaneal articulation, which is the joint between the talus and calcaneus bones in the foot. There are typically three separate components of a valgus deformity at this joint: first, the calcaneus has a valgus position; second, the head of the talus angulates downward; and third, the forefoot is totally abducted in relation to the hind foot. In addition, the Achilles tendon may be pulled laterally due to the outward rotation, or eversion, of the calcaneus.

Pes valgo planus often results from the failure of the arch to form in one or both feet of a child aged two to four, which is the typical age for the natural formation of the arch in the foot. The arch may fail to form due to loose joint connections or baby fat lodged between the foot bones of the child. Pes valgo planus also occurs in adults as a result of Posterior Tibial Tendon Dysfunction (PTTD), one of the more common tendon disorders involving the ankle. The posterior tibial tendon helps support the arch of the foot and provides power to point the foot down and to turn the foot inward. PTTD is typically caused by chronic inflammation, degenerative changes, and occasionally trauma, which lead to stretching, laxity, and eventual rupture of the posterior tibial tendon. People suffering from PTTD often experience tenderness and inflammation along the inner part of the ankle, and may experience weakness when standing on their toes. As the disease progresses, the person may experience loss of the arch of the foot while standing, and the foot tends to turn outward under weight. Late stages of the disease are associated with a flat foot deformity with degenerative changes in the joints below the ankle.

In many cases, the symptoms of pes valgo planus may be treated using conservative measures such as anti-inflammatory medications, rest, ice, shoe inserts or orthotic supports, or even ankle-foot braces. However, in some cases, such measures prove inadequate and the person may continue to experience severe foot or ankle pain or suffer from night cramps, pain when walking and/or standing, or lower back and knee pain. In such cases, a subtalar implant may be used to correct the flatfoot deformity while maintaining mobility of the subtalar joint. The subtalar implant is a small device that is inserted into a small opening in the talocalcaneal joint called the sinus tarsi. The placement of the implant restores the arch by preventing the displacement of the talus and by preventing the foot from rolling-in (pronating). In some cases, tissue may grow around the implant which helps hold the implant in place within the sinus tarsi.

Foot size varies between individuals. Different levels of correction may be required based on foot size and severity of condition. To accommodate these considerations, subtalar implants may come in a variety of sizes. To determine the proper sized implant for a particular person, trial implants may be implanted and removed until the proper size is found for the person.

An example of an existing trial system includes trial implants with threaded holes in the ends that correspond to male threads on the end of a driver handle. A reversed threaded locking device may be included on the driver handle. The reverse threaded locking device may be turned until it jams against the trial implant to lock the trial implant onto the threaded end of the driver handle stem. This may cause problems as the trial implant may not properly lock onto the end of the driver handle. Improper locking may result in the trial implant remaining in the patient when the driver handle is rotated to remove the trial implant.

Another trial system utilizes a "lollipop" design. In this design, each trial implant is permanently mounted to a driver handle. The trial may be implanted and removed using the one piece driver handle. The entire tool would then need to be sterilized or properly disposed. Furthermore, a driver handle is required for each trial implant that is tested. This system can be expensive and bulky.

SUMMARY

In accordance with particular embodiments of the present invention, an implantation tool includes an elongate inner shaft having first and second ends. The tool also includes a first post coupled to the elongate inner shaft proximate the first end of the elongate inner shaft. The first post is configured to engage with a component to couple the component with the elongate inner shaft. The tool further includes a hollow outer shaft defining a longitudinal axial bore within which the elongate inner shaft is disposed. The hollow outer shaft is able to slide along the elongate inner shaft from a first longitudinal position to a second longitudinal position. The hollow outer shaft includes a first locking arm. Moving the hollow outer shaft from the first longitudinal position to the second longitudinal position moves the locking arm closer to the first post.

Another embodiment of the present invention may include a trial implant that includes a conical threaded portion. The implant may also include an unthreaded portion adjacent the conical threaded portion. The unthreaded portion may include a groove having a sliding portion that is approximately parallel to the longitudinal access of the conical threaded portion. The groove may also include a locking slot that is approximately perpendicular to the sliding portion.

Technical advantages of particular embodiments of the present invention may include a trial implant that is prevented from rotating independently from a driver handle. A spring loaded locking mechanism for locking the trial implant to the driver handle may include two positions. In a first position, locking mechanism may securely hold the trial implant on an end of a driver handle. In a second position, the locking mechanism may allow removal and replacement of the trial implant.

Another technical advantage of certain embodiments of the present invention may include the ability to interchange trial implants on a single driver handle. A plurality of trial implants may be provided with each trial implant including a driver handle interface. The driver handle interface of the trial implant may correspond to an interface present on a driver handle. The driver handle may be used to implant and remove each of the trial implants.

A further technical advantage of particular embodiments of the present invention may include a driver handle that is configured to implant and remove a plurality of trial implants and also implant a permanent implant. An end of a driver handle may include more than one interface. One interface may be used to implant a permanent subtalar implant. A second interface of the end of the driver handle may be used to securely couple the driver handle to a trial implant. The interfaces may be arranged such that neither interferes with the operation of the other.

Certain embodiments may provide all, some, or none of these advantages. Certain embodiments may provide one or more other advantages, one or more of which may be apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which:

FIG. 6C illustrates a trial implant and a driver handle in another intermediate stage of coupling the trial implant to the driver handle, in accordance with a particular embodiment of the present invention; and FIG. 6D illustrates a trial implant coupled to a driver handle in accordance with a particular embodiment of the present invention.

DESCRIPTION OF EXAMPLE EMBODIMENTS

According to the present invention, a conical, threaded medical implant is adapted for implantation within a person's body to limit motion in a joint having excessive mobility. In certain embodiments, the medical implant is a subtalar implant adapted for implantation into the person's body and sized to fit within a sinus tarsi of a subtalar joint in the person's body for at least partially preventing displacement of the talus. However, it should be understood that various implants discussed herein may be otherwise used without departing from the scope of the invention.

Figure 1A:
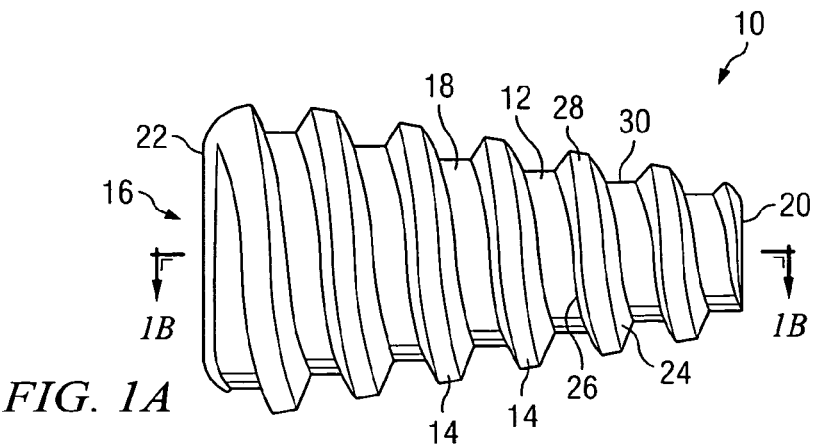
FIGS. 1A-1C illustrate a subtalar implant in accordance with one embodiment of the present invention.
Figure 1B:
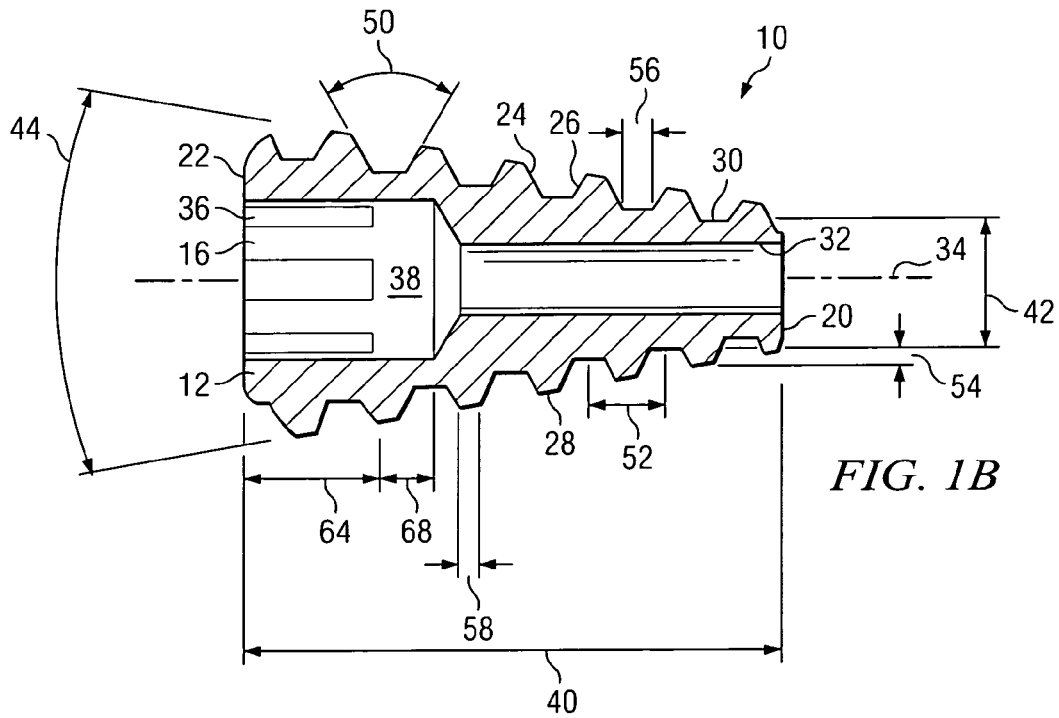
Figure 1C:
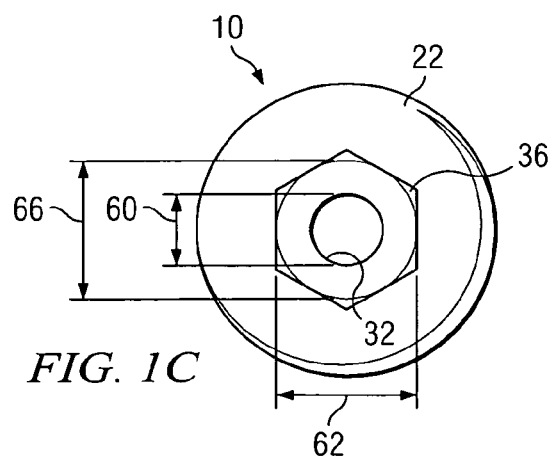

FIGS. 1A-1C illustrate a subtalar implant 10 in accordance with one embodiment of the present invention. In particular, FIG. 1A illustrates an external side view of implant 10, FIG. 1B illustrates a cross-sectional view of implant 10 taken along line A-A of FIG. 1A, and FIG. 1C illustrates an external end view of implant 10. In general, subtalar implant 10 may be inserted into the sinus tarsi of a person suffering from pes valgo planus in a subtalar arthroereisis operation. Once inserted, implant 10 may reduce calcaneal eversion and block excessive displacement of the talus, thus correcting the person's pes valgo planus. In addition, implant 10 may allow normal motion of the subtalar joint while correcting the pes valgo planus, thus allowing the person to function normally.

As shown in FIG. 1A, subtalar implant 10 includes a substantially conical body 12, a plurality of threads 14, and an engagement 16. Threads 14 are formed around the exterior surface 18 of body 12 and extend from a leading end 20 to a trailing end 22 of body 12. Threads 14 are provided to guide the insertion of implant 10 into, and to help secure implant 10 within, the sinus tarsi of a person. Each thread 14 includes a leading flank 24, a trailing flank 26, and a crest 28 connecting leading flank 24 with trailing flank 26. A root 30 is formed between each pair of adjacent threads 14 and connects the leading end 20 of one thread with the trailing end 22 of an adjacent thread 14.

As shown in FIG. 1B, engagement 16 is formed in trailing end 22 of body 12 and is coaxial with a bore 32 extending from leading end 22 of body 12 to engagement 16. Engagement 16 is adapted to receive and be engaged by an implantation tool such that implant 10 may be rotated about a longitudinal axis 34 for the implantation of implant 10 into the sinus tarsi. In this embodiment, engagement 16 comprises a recess having a hexagonal portion 36 integrated with a cylindrical portion 38 such that engagement 16 is adapted to receive and be engaged by a hex-head implantation tool, for example. In other embodiments, engagement 16 may comprise any other suitable types of recesses or other engagements adapted to receive or mate with other implantation tools. For example, engagement 16 may comprise a recess having a cruciform, rectangular, octagonal, or other shape.

FIG. 1B also illustrates various dimensions that define the shape of implant 10. For example, body 12 is at least partially defined by a length 40, a leading end diameter 42, and a taper angle 44. Threads 14 are at least partially defined by a thread angle 50, a pitch 52, a thread height 54, a root width 56, and a crest width 58. A variety of implants 10 may be formed in various sizes and having various values for the dimensions listed above. For example, length 40, leading end diameter 42, and taper angle 44 may be appropriately sized to fit within the sinus tarsi of a person. Since the sinus tarsi of different people may have a range of sizes, a variety of implants 10 may be provided having a range of lengths 40, leading end diameters 42, and taper angles 44 such that an appropriate implant 10 may be selected for each person based on the size and shape of that person's sinus tarsi. For example, for various implants 10, length 40 may range from approximately 0.39 inches to approximately 0.78 inches and leading end diameter 42 may range from approximately 0.078 inches to approximately 0.39 inches. In the embodiment shown in FIGS. 1A-1C, length 40 is approximately 0.59 inches and leading end diameter 42 is approximately 0.163 inches.

Similarly, a range of taper angles 44 may be used in various implants 10 to correspond with a range of taper angles of the sinus tarsi of various people. For example, in a variety of implants 10, taper angle 44 may range from 10 to 30 degrees. In certain embodiments, taper angle 44 may range from approximately 15 to 20 degrees. In the embodiment shown in FIGS. 1A-1C, taper angle 44 is approximately 18 degrees. By providing implants 10 having a range of taper angles 44, an implant 10 may be selected for a particular person that has a taper angle 44 substantially equal to the taper of the sinus tarsi of that person. Thus, implant 10 may fit more precisely or snugly within the tapered sinus tarsi as compared with prior cylindrical or other non-tapered implants. As a result, the likelihood of pressure points between implant 10 and the surrounding bones (including the talus and the calcaneus) which may cause pain or even result in insert 10 popping out of the sinus tarsi, is reduced as compared with prior cylindrical or other non-tapered implants.

The dimensions defining threads 14 may be selected based on a number of objectives, such as to provide implant 10 that may be easily threaded into the sinus tarsi and adequately secured in place within the sinus tarsi, and to limit or avoid pain to the patient, for example. In certain embodiments, threads 14 may be formed such that they are sharp enough to adequately secure implant 10 in place within a person's sinus tarsi, yet not sharp enough to cause pain to the person. In particular, the ratio of crest width 58 to one or more other thread dimensions, such as pitch 52 or thread height 54 for example, may be selected in order to provide these objectives. For example, the ratio of crest width 58 to pitch 52 may be greater than or approximately equal to 0.15. In certain embodiments, the ratio of crest width 58 to pitch 52 is between approximately 0.2 and 0.4. In the embodiment shown in FIGS. 1A-1C, the ratio of crest width 58 to pitch 52 is approximately 0.25. As another example, the ratio of crest width 58 to thread height 54 may be greater than or approximately equal to 0.3. In certain embodiments, the ratio of crest width 58 to thread height 54 is between approximately 0.5 and 1.0. In the embodiment shown in FIGS. 1A-1C, the ratio of crest width 58 to thread height 54 is approximately 0.72.

Other dimensions of threads 14 may similarly be selected based on various objectives of insert 10, such as those discussed above. For example, thread angle 50 may be between approximately 45 and 75 degrees. In the embodiment shown in FIGS. 1A-1C, thread angle 50 is approximately 60 degrees. As another example, pitch 52 may be between approximately 0.050 and 0.200 inches. In certain embodiments, pitch 52 is between approximately 0.080 and 0.120 inches. In the embodiment shown in FIGS. 1A-1C, pitch 52 is approximately 0.090 inches. In certain other embodiments, pitch 52 is approximately 0.100 inches. As yet another example, thread height 54 may be between approximately 0.010 and 0.060 inches. In certain embodiments, thread height 54 is between approximately 0.020 and 0.050inches. In the embodiment shown in FIGS. 1A-1C, thread height 54 is approximately 0.032 inches. In certain other embodiments, thread height 54 is approximately 0.041 inches. As yet another example, root width 56 may be between approximately 0.020 and 0.040 inches. In the embodiment shown in FIGS. 1A-1C, root width 56 is approximately 0.030 inches.

Taken together, FIGS. 1B and 1C illustrate engagement 16 and bore 32 formed in body 12 of implant 10. Bore 32 is at least partially defined by a bore diameter 60. Hexagonal portion 36 of engagement 16 is defined by a width 62 and depth 64 and cylindrical portion 38 engagement 16 is defined by a diameter 66 and depth 68. In the embodiment shown in FIGS. 1A-1C, hexagonal portion 36 has a width 62 and depth 64 of approximately 0.159 inches and 0.15 inches, respectively, while cylindrical portion 38 has a diameter 66 and depth 68 of approximately 0.166 inches and 0.20 inches, respectively. As shown in FIG. 1C, bore 32 has a diameter between 0.067 and 0.072 inches.

Implant 10 may be formed from any one or more materials suitable for forming medical implants, such as materials that have high strength-to-weight ratios and that are inert to human body fluids. In certain embodiments, implant 10 is formed from one or more titanium alloys, which provide several benefits. For example, titanium alloys are relatively lightweight, provide adequate strength for withstanding forces typically experienced by an implanted medical implant, are inert to human body fluids, and are visible in radiographs of the implant region. In particular embodiment, implant 10 is formed from the titanium based alloy Ti6Al4V ELI (per ASTM F136), which provides a desirable combination of benefits, such as those discussed above. In certain other embodiments, implant 10 is formed from one or more resorbable polymers, such as polylactides, polyglycolide, glycolide/lactide copolymers or other copolymers for example, or one or more implantable plastics, such as polyethylene or acetyl copolymers for example.

Figure 2:
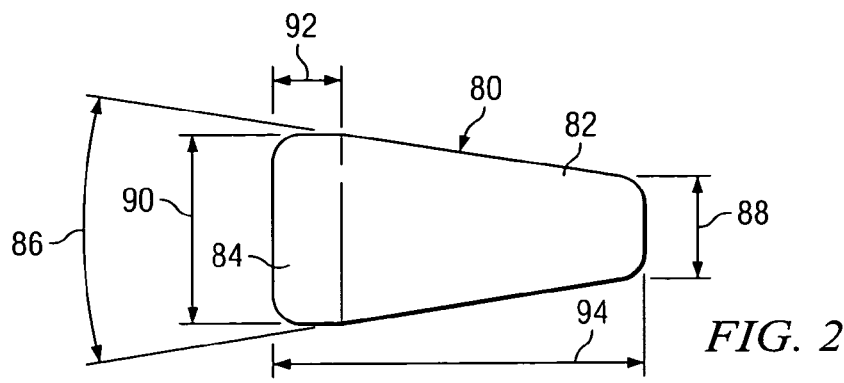
FIG. 2 illustrates a detail of an example slug used to form the implant shown in FIGS. 1A-1C.

FIG. 2 illustrates a detail of a slug 80 used to form implant 10 according to one embodiment of the present invention. In particular, threads 14 are formed in slug 80 to form implant 10 shown in FIGS. 1A-1C. As shown in FIG. 1, slug 80 includes a conical portion 82 and a cylindrical portion 84. Cylindrical portion 84 may be provided for the machining of implant 10. For example, cylindrical portion 84 of slug 80 may be gripped by various machining tools during the machining of slug 80 to form implant 10.

Slug 80 is at least partially defined by a taper angle 86, a leading end diameter 88, a cylindrical portion diameter 90, a cylindrical portion length 92, and an overall length 94. In the embodiment shown in FIG. 2 that is used to form implant 10 shown in FIGS. 1A-1C, taper angle 86 is approximately 18 degrees, leading end diameter 88 is approximately 0.163 inches, cylindrical portion diameter 90 is approximately 0.315 inches, cylindrical portion length 92 is approximately 0.110 inches, and overall length 94 is approximately 0.59 inches.

Figure 3A:
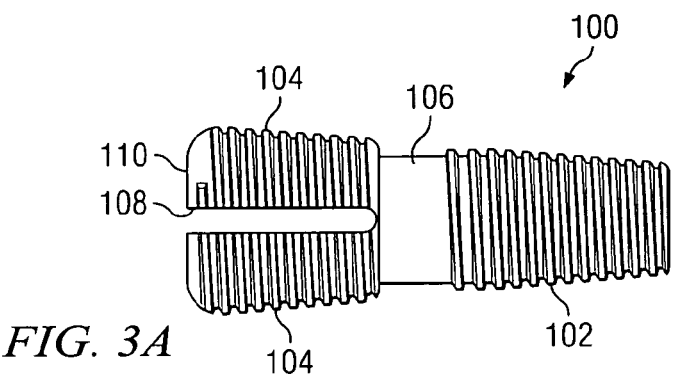
FIGS. 3A-3C illustrate various subtalar implants according to other embodiments of the present invention.
Figure 3B:
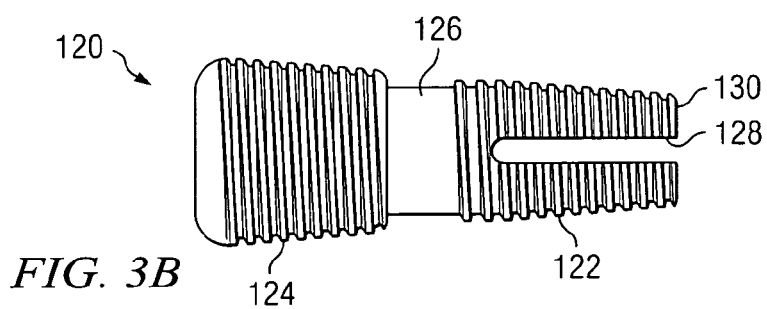
Figure 3C:
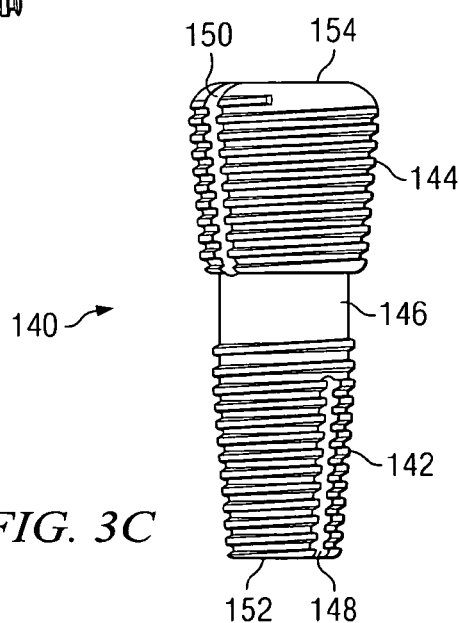

FIGS. 3A-3C illustrate various subtalar implants according to other embodiments of the present invention. As shown in FIG. 3A, implant 100 includes a leading conical portion 102, a trailing conical portion 104, and a cylindrical portion 106 connecting leading conical portion 102 with trailing conical portion 104. Cylindrical portion 106 may be used to hold implant 100 during the machining of implant 100. Implant 100 also includes a slot 108 extending across the diameter of trailing conical portion 104 and extending from a trailing end 110 of implant 100 substantially or completely through the length of trailing conical portion 104. Slot 108 may provide increased elasticity and resiliency to implant 100, which may reduce the likelihood of structural failure of implant 100 when subjected to various forces and stresses associated with being implanted in a person's sinus tarsi. For example, slots 108 may dissipate a portion of various impact forces experienced by implant 100, such as impact forces caused by the person walking or running.

As shown in FIG. 3B, implant 120 includes a leading conical portion 122, a trailing conical portion 124, a cylindrical portion 126 connecting leading conical portion 122 with trailing conical portion 124, and a slot 128. However, unlike slot 108 of implant 100, slot 128 of implant 120 extends across the diameter of leading conical portion 122 and extends from a leading end 130 of implant 120 substantially or completely through the length of leading conical portion 122. As discussed above regarding slot 108 of implant 100, slot 128 of implant 120 may provide increased elasticity to implant 120, which may reduce the likelihood of structural failure of implant 120 when subjected to various forces and stresses associated with being implanted in a person's sinus tarsi.

As shown in FIG. 3C, implant 140 includes a leading conical portion 142, a trailing conical portion 144, a cylindrical portion 146 connecting leading conical portion 142 with trailing conical portion 144, a first slot 148, and a second slot 150. First slot 148 extends across the diameter of leading conical portion 142 and extends from a leading end 152 of implant 140 substantially or completely through the length of leading conical portion 142. Second slot 150 extends across the diameter of trailing conical portion 144 and extends from a trailing end 154 of implant 140 substantially or completely through the length of trailing conical portion 144. In the embodiment shown in FIG. 3C, first slot 148 and second slot 150 are formed substantially perpendicular to one another. As discussed above regarding slots 108 and 128, slots 148 and 150 of implant 140 may provide increased elasticity to implant 140, which may reduce the likelihood of structural failure of implant 140 when subjected to various forces and stresses associated with being implanted in a person's sinus tarsi.

Figure 4:
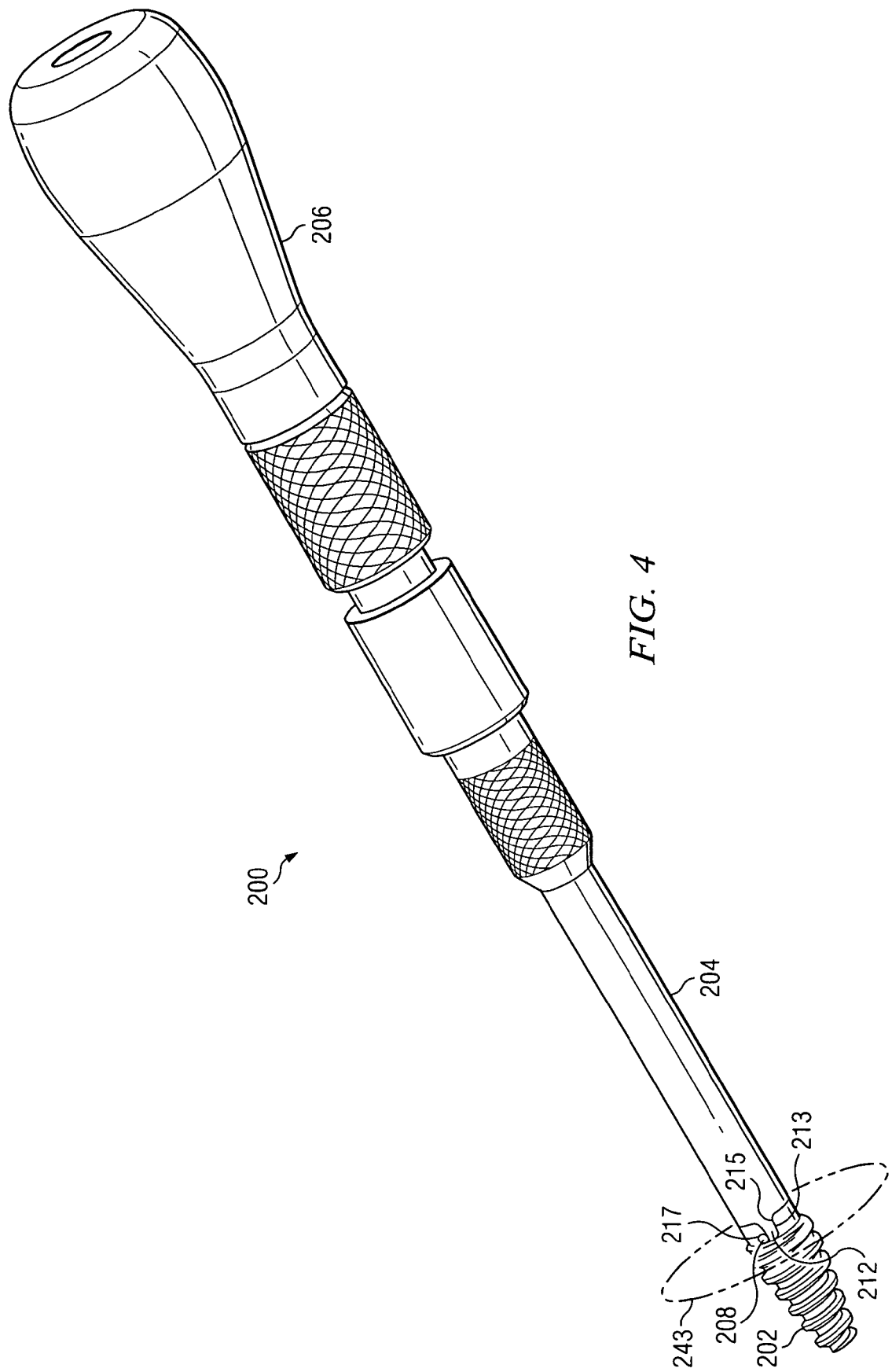
FIG. 4 illustrates an implantation system including a trial implant and a driver handle in accordance with a particular embodiment of the present invention.

FIG. 4 illustrates an implantation assembly 200 that may be used for implanting and removing one or more of a plurality of trial implants and for implanting a permanent implant. Implantation assembly 200 includes trial implant 202, implantation tool 204, and driver handle 206. Implantation tool 204 may couple trial implant 202 to driver handle 206 such that when driver handle 206 is rotated, trial implant 202 rotates with driver handle 206. An interface between trial implant 202 and implantation tool 204 is designed such that trial implant 202 is securely coupled to implantation tool 204 when components of implantation tool 204 are in a first configuration, and trial implant 202 may be easily removed from implantation tool 204 when components of implantation tool 204 are in a second configuration. While only the first configuration of implantation tool 204 is illustrated in FIG. 4, the second configuration of implantation tool 204 will be illustrated and described with reference to FIGS. 6A, 6B, and 6C. Furthermore, while the discussion below focuses on using implantation tool 204 with trial implants 202, particularly with respect to subtalar implants, the interface between implantation tool 204 and trial implants 202 could potentially be used as an interface between any tool and corresponding component, whether medical in nature or otherwise, to removably couple the component to the tool.

In the illustrated embodiment, trial implant 202 includes a groove 213. Groove 213 includes a sliding portion 215 and a locking slot 217. Locking slot 217 may be approximately perpendicular to sliding portion 215. Correspondingly, implantation tool 204 includes a post 208 and a locking arm 212. In the first configuration of the components of implantation tool 204, post 208 may reside in locking slot 217 of groove 213, and locking arm 212 may reside in sliding portion 215 of groove 213. The operation of the various parts of trial implant 202 and implantation tool 204 will be described in more detail with reference to FIGS. 6A-D. It should be understood that trial implant 202 may include any number of grooves 213 and implantation tool 204 may include any number of corresponding posts 208 and locking arms 212 to suit a particular application. For example, in particular embodiments, two grooves, posts, and locking arms may be utilized.

Figure 5:
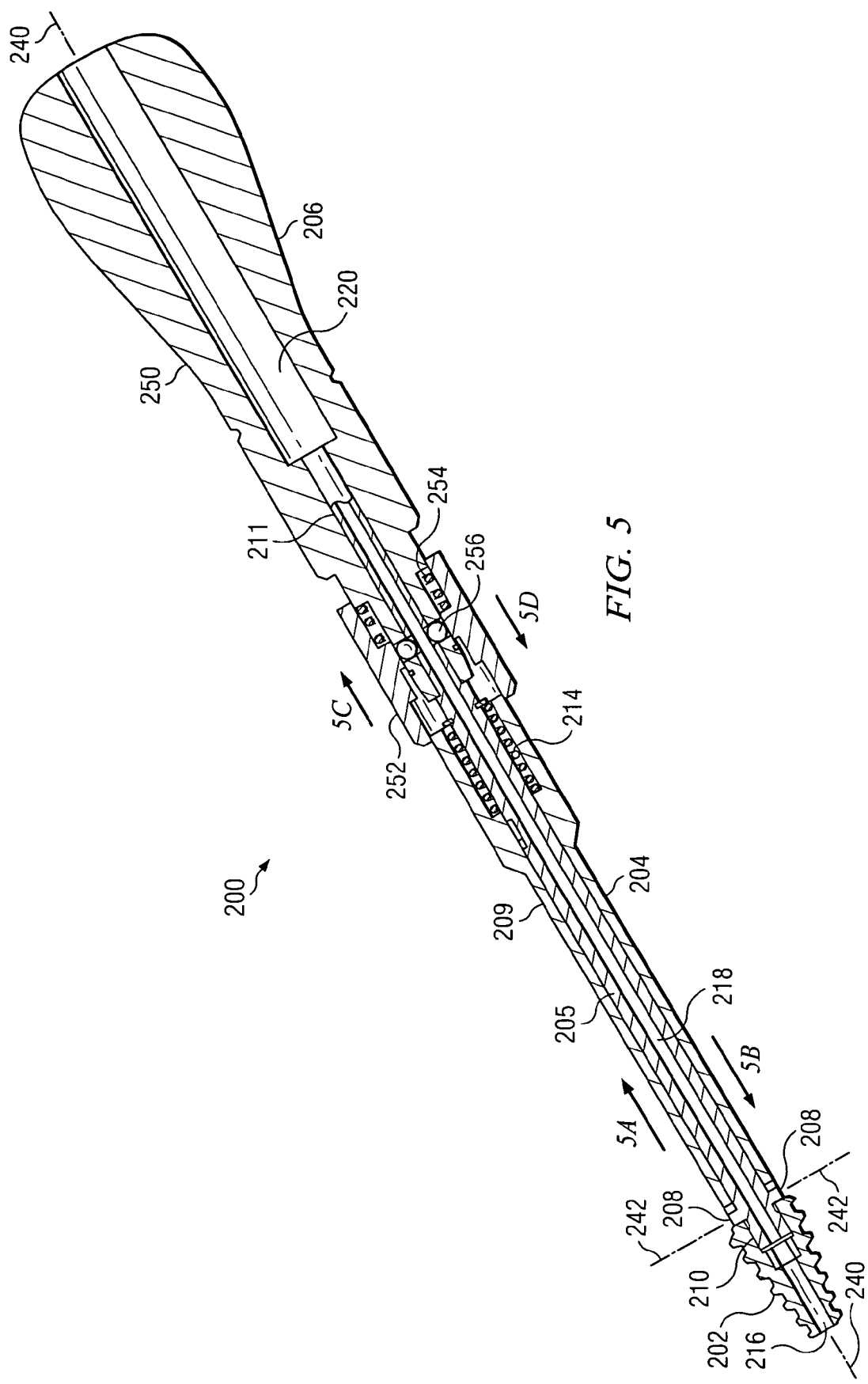
FIG. 5 illustrates a cross section of the implantation tool of FIG. 4 in accordance with a particular embodiment of the present invention.

FIG. 5 illustrates a cut away view of implantation assembly 200 along the length of implantation assembly 200 perpendicular to longitudinal axis 240 of implantation assembly 200. Trial implant 202 is illustrated as coupled to implantation tool 204, and implantation tool 204 is illustrated as coupled to driver handle 206.

Implantation tool 204 includes an elongate inner shaft 205 having a first end 210 and a second end 211. Inner shaft 205 resides within a hollow bore of hollow outer shaft 209. Outer shaft 209 is able to slide along inner shaft 205 in the directions indicated by arrows 5A and 5B. The sliding motions of outer shaft 209 may be approximately parallel to longitudinal axis 240. Outer shaft 209 is illustrated in a first longitudinal position relative to inner shaft 205. Outer shaft 209 may be moved in the direction of arrow 5A to move outer shaft 209 to a second longitudinal position relative to inner shaft 205. Outer shaft 209 may be moved from the second longitudinal position back to the first longitudinal position by sliding outer shaft 209 in the direction indicated by arrow 5B. Outer shaft 209 may be biased in the direction of arrow 5B by a spring 214. Spring 214 may maintain outer shaft 209 in the first longitudinal position until a force is applied to outer shaft 209 in the direction of arrow 5A to direct the outer shaft to the second longitudinal position.

In the first longitudinal position of outer shaft 209, trial implant 202 is securely coupled to implantation tool 204 by post 208 and locking arm 212 (see FIG. 4). Locking arms 212 may be integral to outer shaft 209. Posts 208 may be coupled to inner shaft 205. This arrangement allows locking arms 212 to be moved along with outer shaft 209 to the second longitudinal position while posts 208 remain in place. In the first longitudinal position of outer shaft 209, locking arms 212 and posts 208 may at least partially reside in a common radial plane, such as radial plane 243 illustrated in FIG. 4, perpendicular to longitudinal access 240. As outer shaft 209 is moved to the second longitudinal position, locking arms 212 are longitudinally separated from posts 208. When locking arms 212 have been moved along with outer shaft 209 to the second longitudinal position, implantation tool 204 may be rotated such that posts 208 move from locking slot 217 of groove 213 into the sliding portion 215 of groove 213. The trial implant 202 may then be removed from implantation tool 204. The removal and installation of trial implants 202 from implantation tool 204 will be described in more detail with reference to FIGS. 6A-D.

In the embodiment of FIG. 5, two posts 208 are illustrated. In the illustrated embodiment, posts 208 have a common longitudinal axis 242. In other embodiments, more than two posts may be arranged around inner shaft 205 and such posts may or may not share a common longitudinal axis. Additionally, posts 208 are illustrated as having circular cross sections, however, cross sections of posts in other embodiments may be any suitable shape. Furthermore, the lengths and configurations of posts in other embodiments may vary from the illustrated lengths and configurations. As illustrated, posts 208 extend radically outward from inner shaft 205 in a straight-line manner. However, posts in other embodiments may be curved or flared as appropriate for a particular application.

Posts 208 may be coupled to inner shaft 205 in any appropriate manner. In particular embodiments, for example, posts 208 may be integral to inner shaft 205. In this embodiment, posts 208 may be machined from the same piece of material as inner shaft 205. As another example, posts 208 may be screwed into receiving holes on inner shaft 205.

Trial implant 202 also includes a recessed portion in one end that is operable to receive a first end 210 of inner shaft 205. As illustrated in more detail in FIG. 6A, first end 210 may be adapted to couple implantation tool 204 to a permanent implant, such as, for example, the implant illustrated in FIG. 1C. The ability of trial implant 202 to fit over first end 210 may enable implantation tool 204 to be used both for implanting and removing trial implants 202 and for implanting permanent implants, such as, for example, the implant illustrated in FIG. 1C. In other embodiments, trial implants may have any appropriate size, shape, and configuration to suit a particular application. In particular embodiments, trial implants may have sizes, shapes, and configurations corresponding to the permanent subtalar implants illustrated in FIGS. 1A-C and 3A-C. In other embodiments, trial implants may be configured as trials for any suitable type of implant, whether a subtalar implant or otherwise.

Driver handle 206 may be coupled to implantation tool 204 at second end 211 of implantation tool 204. Driver handle 206 may include a release 252 that may be moved approximately parallel to longitudinal access 240 in the directions indicated by arrows 5C and 5D. As illustrated, implantation tool 204 may be securely coupled to driver handle 206 by bearings 256 of driver handle 206. Bearings 256 may be securely seated in corresponding dimples present in second end 211 of implantation tool 204. Moving release 252 in the direction indicated by arrow 5C will allow bearings 256 to become unseated from their corresponding dimples in second end 211 of implantation tool 204 and may allow implantation tool 204 to be removed from driver handle 206. Release 252 may be biased towards the direction indicated by arrow 5D by spring 254. Spring 254 may thereby maintain bearings 256 in the corresponding dimples of second end 211 of implantation tool 204 until a force is imparted on release 252 in the direction of arrow 5C. Utilizing the configuration illustrated in FIG. 5, implantation tool 204 may be easily removed from driver handle 206 and any tool having the proper configuration to couple with driver handle 206 may be substituted for implantation tool 204.

Driver handle 206 may also include a handle 250. Handle 250 may allow a user of implantation assembly 200 to grip and rotate implantation assembly 200. By rotating handle 250, trial implant 202 may be implanted and removed. When a permanent implant is substituted for trial implant 202, rotating handle 250 may rotate and implant the permanent implant. In certain embodiments, handle 250 may be appropriately sized to fit an average sized hand. In other embodiments, handle 250 may be interchangeable with different sized handles to maximize comfort and utility for a particular user.

Implantation assembly 200 may also include a longitudinal bore passing through each of its components. Trial implant 202 may include longitudinal bore 216, implantation tool 204 may include longitudinal bore 218, and driver handle 206 may include longitudinal bore 220. The longitudinal bores 216, 218, and 220 may allow implantation assembly 200 to slide over a guide wire that has been inserted into an implantation site, such as the sinus tarsi, to aid in proper alignment and placement of both trial implant 202 and a permanent implant. The components of implantation assembly 200 may be assembled either before or after the components have been slid over the guide wire.

Figure 6A:
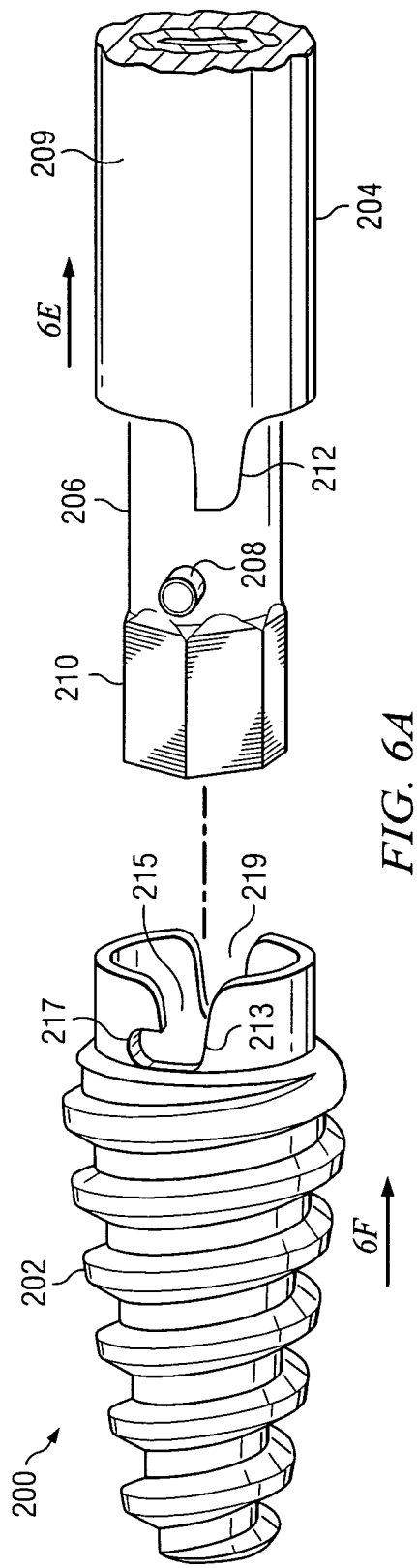
FIG. 6A illustrates an interface between a trial implant and a driver handle when the trial implant and the driver handle are not coupled to one another, in accordance with a particular embodiment of the present invention.
Figure 6B:
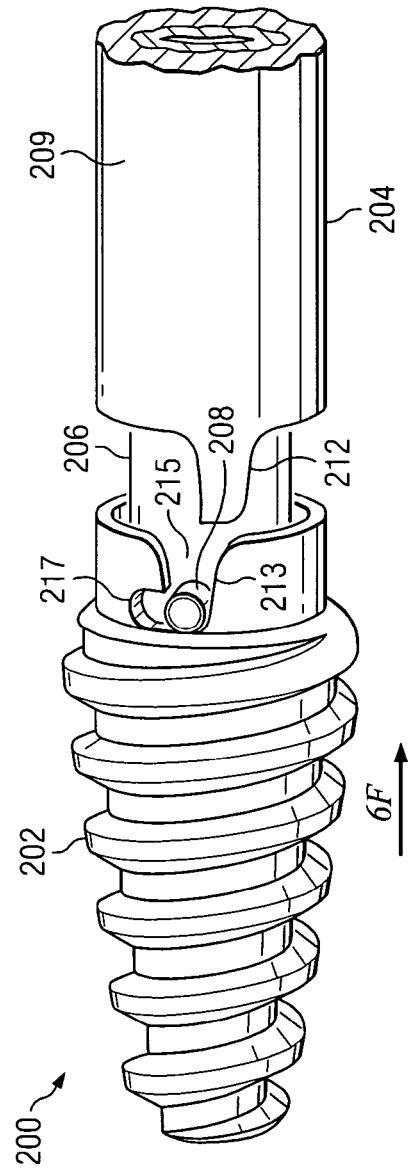
FIG. 6B illustrates a trial implant and a driver handle in an intermediate stage of coupling the trial implant to the driver handle, in accordance with a particular embodiment of the present invention.

FIGS. 6A-D illustrate the process of installing and removing a trial implant 202 from implantation tool 204. In FIG. 6A, trial implant 202 is illustrated as being separate from implantation tool 204, and outer shaft 209 is illustrated in the second longitudinal position relative to inner shaft 205. Likewise, locking arm 212 is illustrated as longitudinally separated from post 208. As illustrated by FIG. 6B, trial implant 202 may be positioned on first end 210 of implantation tool 204. As trial implant 202 is moved in the direction indicated by arrow 6F, post 208 will slide within sliding portion 215 of groove 213 until post 208 abuts the intersection of sliding portion 215 and locking slot 217.

FIG. 6C illustrates rotating trial implant 202 in the direction illustrated by arrow 6G until post 208 has come to reside in locking slot 217 of groove 213. FIG. 6D illustrates outer shaft 209 moving to the first longitudinal position as illustrated by arrow 6H. As outer shaft 209 moves to the first longitudinal position, locking arm 212 slides within sliding portion 215 of groove 213 until locking arm 212 resides within sliding portion 215. In this configuration, locking arm 212 prevents further rotation of trial implant 202. Locking arm 212 also maintains post 208 within locking slot 217 of groove 213. While post 208 resides in locking slot 217, trial implant 202 may not be separated from implantation tool 204. In this manner, trial implant 202 may be securely coupled to implantation tool 204. Once securely coupled to implantation tool 204, trial implant 202 may be implanted into a patient by rotating implantation tool 204. A judgment may be made on the appropriateness of trial implant 202 for the patient and then trial implant 202 maybe removed from the patient. Trial implant 202 may be removed by rotating implantation tool 204 in the opposite direction than it was rotated to implant trial implant 202. Once trial implant 202 has been removed from the patient, trial implant 202 may be removed from implantation tool 204 and, if trial implant 202 was not a good fit for the patient, a different sized or shaped trial implant may be coupled to implantation tool 204 for implantation into the patient. If the trial implant was an appropriate fit for the patient, trial implant 202 may be removed from implantation tool 204 and a permanent implant corresponding to trial implant 202 may be implanted in the patient using implantation tool 204.

Removing trial implant 202 from implantation tool 204 may be accomplished by reversing the steps illustrated in FIGS. 6A-D. Outer shaft 209 may be moved to the second longitudinal position and trial implant 202 may be rotated such that post 208 resides in sliding portion 215. Trial implant 202 may then be removed from the end of implantation tool 204 by moving trial implant 202 longitudinally away from implantation tool 204. Once trial implant 202 has been removed from implantation tool 202, outer shaft 209 may be released to return to the first longitudinal position.

FIG. 6A also illustrates first end 210 of implantation tool 204 as being configured to interface with a permanent implant. In the illustrated embodiment, first end 210 has a hexagonal shape that corresponds to a hexagonal recess in a permanent implant, such as the implant illustrated in FIG. 1C. In alternative embodiments, first end 210 may be shaped as a triangle, square, rectangle, octagon, star, blade, cross, or any other shape to fit a particular permanent implant. First end 210 will not interfere with the interface between trial implant 202 and implantation tool 204 because first end 210 may reside in hollow recess 219 when trial implant 202 is positioned on implantation tool 204. In this manner, implantation tool 204 may be used both to implant and remove trial implants and also to implant permanent implants. Implantation tool 204 may be used with a plurality of trial implants having different sizes and shapes so that the proper trial implant for a particular patient may be discovered. Trial implants may be installed on and removed from implantation tool 204 until the proper size implant is discovered. Once the proper trial implant is known, implantation tool 204 may be used to implant the permanent implant corresponding to the proper trial implant.

Although the present invention has been described with several embodiments, a number of changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:
1. A implantation assembly, comprising an implantation tool and a component, wherein:
the implantation tool comprises:
an elongate inner shaft having a first end;
a first post coupled to the elongate inner shaft proximate the first end of the elongate inner shaft, the first post configured to fit into a locking slot of the component to couple the component with the elongate inner shaft;

a hollow outer shaft defining a longitudinal axial bore within which the elongate inner shaft is disposed, the hollow outer shaft able to slide along the elongate inner shaft from a first longitudinal position to a second longitudinal position, the hollow outer shaft including a first locking arm operable to fit into a sliding portion of the component in a manner which prevents the component from rotating relative to the first post once the first post is positioned in the locking slot; and the component comprises:

an end with a recessed central portion adapted to fit over the first end of the elongate inner shaft; and a groove having the sliding portion and the locking slot, the locking slot configured to rotate onto the first post;

the component has first and second orientations relative to the elongate inner shaft, wherein in the first orientation of the component relative to the elongate inner shaft the sliding portion of the groove is in a position to receive the post and wherein in the second orientation of the component relative to the elongate inner shaft the first post resides in the locking slot of the groove;

the sliding portion of the groove is disposed perpendicular to the locking slot; and the locking arm is operable to prevent the component from rotating relative to the first post once the first post is positioned in the locking slot be closing off the sliding portion from the locking slot.

2. The assembly of claim 1, wherein when the component is in the second orientation relative to the elongate inner shaft and the hollow outer shaft is in the first longitudinal position, the first locking arm of the hollow outer shaft resides in the sliding portion of the groove of the component and prevents the component from rotating from the second orientation to the first orientation.

3. The assembly of claim 1, wherein when the component is in the first orientation relative to the elongate inner shaft and the hollow outer shaft is in the second longitudinal position, the component is separable from the first end of the elongate inner shaft.

4. The assembly of claim 1, wherein the component is securely coupled to the elongate inner shaft when the hollow outer shaft is in the first longitudinal position and the component is in the second orientation.

5. The assembly of claim 1, wherein portions of the first locking arm and portions of the first post reside in a common radial plane perpendicular to a longitudinal axis of the elongate inner shaft when the hollow outer shaft is in the first longitudinal position, and the first locking arm and the first post are adapted to separate longitudinally as the hollow outer shaft is moved to the second longitudinal position.

6. The assembly of claim 1, further comprising a spring biasing the outer shaft toward the first longitudinal position.

7. The assembly of claim 1, wherein the elongate inner shaft defines a hollow longitudinal bore approximately parallel to the longitudinal axis, the hollow longitudinal bore operable to accept a guide wire.

8. The assembly of claim 1, wherein:

the implantation tool further comprises a second post coupled to the elongate inner shaft proximate the first end of the elongate inner shaft, the second post arranged on the elongate inner shaft radially opposite from the first post; and the hollow outer shaft further comprises a second locking arm, portions of the first and second locking arms and portions of the first and second posts residing in a common radial plane perpendicular to the longitudinal axis of the elongate inner shaft when the hollow outer shaft is in the first longitudinal position.

9. The assembly of claim 8, wherein the first and second posts have a common longitudinal axis and the longitudinal axis of the first and second posts is generally perpendicular to the longitudinal axis of the elongate inner shaft.

10. The assembly of claim 1, wherein the first end of the elongate inner shaft is adapted to mate with the component such that the component is rotated when the elongate inner shaft is rotated.

11. The assembly of claim 10, wherein the first end of the elongate inner shaft includes a length with a hexagonally shaped cross section and the component includes a corresponding hexagonally shaped recess.

12. The assembly of claim 1, wherein a second end of the elongate inner shaft includes a length having one or more dimples for securing the tool to a handle, the handle utilizing a release mechanism including a spring and a ball bearing for releasably coupling the elongate inner shaft to the handle.

13. A implantation assembly, comprising an implantation tool and a component, wherein:

the implantation tool comprises:

an elongate inner shaft having a first end;

a first post coupled to the elongate inner shaft proximate the first end of the elongate inner shaft, the first post configured to engage with the component to couple the component with the elongate inner shaft;

a hollow outer shaft defining a longitudinal axial bore within which the elongate inner shaft is disposed, the hollow outer shaft able to slide along the elongate inner shaft from a first longitudinal position to a second longitudinal position, the hollow outer shaft including a first locking arm; and the component comprises a trial implant, the trial implant comprising:

an end with a recessed central portion adapted to fit over the first end of the elongate inner shaft; and a groove having a sliding portion and a locking slot the component having first and second orientations relative to the elongate inner shaft, wherein in the first orientation of the component relative to the elongate inner shaft the sliding portion of the groove is in a position to receive the post and wherein in the second orientation of the trial implant relative to the elongate inner shaft the first post resides in the locking slot of the groove;

a conical threaded portion; and an unthreaded portion adjacent the conical threaded portion, the unthreaded portion including the groove, the sliding portion of the groove approximately parallel to a longitudinal axis of the conical threaded portion and the locking slot of the groove approximately perpendicular to the sliding portion.

14. The assembly of claim 13, wherein the conical threaded portion defines a hollow longitudinal bore approximately parallel to the longitudinal axis, the hollow longitudinal bore operable to accept a guide wire.

15. The assembly of claim 13, wherein the conical threaded portion comprises at least one thread helically traversing an exterior surface of the conical threaded portion, the thread comprising:

a crest with a substantially flat surface and having a substantially constant thread height; and a leading flank spanning from the crest to a thread root and a trailing flank spanning from the crest to the thread root, the leading flank separated from the trailing flank by a narrowing clearance therebetween.

16. The assembly of claim 15, wherein:
the circumference of the exterior surface tapers uniformly from the first end to the second end according to a predetermined taper angle;

the leading flank and the trailing flank define a constant thread angle therebetween; and the direction of incline of the leading flank is opposite the direction of incline of the trailing flank.

* * * * *